US009511132B2

(12) United States Patent
Contorni

(10) Patent No.: US 9,511,132 B2
(45) Date of Patent: Dec. 6, 2016

(54) MIXING LYOPHILISED MENINGOCOCCAL VACCINES WITH D-T-PA VACCINES

(75) Inventor: Mario Contorni, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 40 days.

(21) Appl. No.: 13/139,021

(22) PCT Filed: Dec. 11, 2009

(86) PCT No.: PCT/IB2009/007926
§ 371 (c)(1),
(2), (4) Date: Sep. 7, 2011

(87) PCT Pub. No.: WO2010/067201
PCT Pub. Date: Jun. 17, 2010

(65) Prior Publication Data
US 2011/0311575 A1 Dec. 22, 2011

(30) Foreign Application Priority Data
Dec. 11, 2008 (GB) .................................. 0822633.4

(51) Int. Cl.
*A61K 39/018* (2006.01)
*A61K 39/095* (2006.01)
*A61K 39/02* (2006.01)
*A61K 39/05* (2006.01)
*A61K 39/08* (2006.01)
*A61K 39/00* (2006.01)

(52) U.S. Cl.
CPC ......... *A61K 39/099* (2013.01); *A61K 39/0018* (2013.01); *A61K 39/05* (2013.01); *A61K 39/08* (2013.01); *A61K 39/095* (2013.01); *A61K 2039/55505* (2013.01); *A61K 2039/6037* (2013.01); *A61K 2039/70* (2013.01)

(58) Field of Classification Search
CPC ...... A61K 39/00; A61K 39/05; A61K 39/11; A61K 39/116; A61K 2039/55505; A61K 39/10; A61K 39/13; A61K 39/095
USPC ................................ 424/201.1, 254.1, 203.1
See application file for complete search history.

(56) References Cited

U.S. PATENT DOCUMENTS

| 4,578,270 | A  * | 3/1986  | Csizer et al. ............... 424/203.1 |
| 6,399,076 | B2 * | 6/2002  | Vose et al. ................. 424/254.1 |
| 6,696,065 | B1 * | 2/2004  | Fahim et al. ............... 424/254.1 |
| 7,927,858 | B2 * | 4/2011  | Mayeresse .................... 435/243 |
| 8,007,807 | B2 * | 8/2011  | Borkowski ......... A61K 39/0018 424/184.1 |
| 8,007,818 | B2 * | 8/2011  | Garcon ................ A61K 39/102 424/193.1 |
| 8,298,983 | B2 * | 10/2012 | Takeshima et al. .......... 502/235 |
| 8,361,477 | B2 * | 1/2013  | Borkowski ......... A61K 39/0018 424/184.1 |
| 8,409,587 | B2 * | 4/2013  | Mayeresse et al. ....... 424/201.1 |
| 8,444,992 | B2 * | 5/2013  | Borkowski ......... A61K 39/0018 424/184.1 |
| 8,529,908 | B2   | 9/2013  | Marshall |
| 8,551,451 | B2 * | 10/2013 | Jain et al. ...................... 424/9.2 |
| 8,574,589 | B2 * | 11/2013 | Lease .......................... 424/203.1 |
| 8,623,380 | B2 * | 1/2014  | Florent et al. ............. 424/203.1 |
| 8,753,651 | B2 * | 6/2014  | Costantino .................. 424/250.1 |
| 8,778,275 | B2 * | 7/2014  | Rueckl et al. ................. 422/224 |
| 8,784,826 | B2 * | 7/2014  | Borkowski ........ A61K 39/0018 424/184.1 |
| 8,802,111 | B2 * | 8/2014  | Contorni ............. A61K 39/099 424/227.1 |
| 8,883,166 | B2 * | 11/2014 | Contorni ............. A61K 39/095 424/194.1 |
| 8,956,625 | B2 * | 2/2015  | De Hemptinne ...... A61K 39/13 424/196.11 |
| 9,040,058 | B2 * | 5/2015  | Blackkolb ............. C07K 14/34 424/166.1 |
| 2003/0202978 | A1 * | 10/2003 | Maa et al. .................. 424/184.1 |
| 2004/0208898 | A1 * | 10/2004 | Florent et al. ............. 424/202.1 |
| 2005/0002948 | A1   | 1/2005  | Ryall et al. |
| 2005/0106181 | A1 * | 5/2005  | Constantino ............... 424/238.1 |
| 2006/0051378 | A1 * | 3/2006  | Guidice et al. ............. 424/241.1 |
| 2006/0121059 | A1 * | 6/2006  | Garcon et al. ............. 424/256.1 |
| 2006/0127414 | A1 * | 6/2006  | Mayeresse et al. ....... 424/201.1 |
| 2007/0298052 | A1 * | 12/2007 | Mayeresse ................. 424/217.1 |
| 2009/0035326 | A1 * | 2/2009  | Contorni et al. ........ 424/196.11 |
| 2009/0130146 | A1 * | 5/2009  | Broeker ..................... 424/217.1 |
| 2009/0155305 | A1 * | 6/2009  | Contorni .................... 424/201.1 |
| 2009/0181050 | A1 * | 7/2009  | Kim et al. ................. 424/203.1 |
| 2009/0214586 | A1   | 8/2009  | Contorni et al. |
| 2010/0040647 | A1 * | 2/2010  | De Hemptinne et al. ......................... 424/197.11 |
| 2013/0004536 | A1   | 1/2013  | Borkowski |
| 2013/0122040 | A1 * | 5/2013  | Blackkolb ............. C07K 14/34 424/201.1 |
| 2013/0236492 | A1 * | 9/2013  | Baudner ............ A61K 39/0018 424/201.1 |
| 2015/0037368 | A1 * | 2/2015  | Garcon ................ A61K 39/102 424/197.11 |
| 2015/0125486 | A1 * | 5/2015  | Bufali ................ A61K 39/0018 424/201.1 |
| 2015/0224185 | A1 * | 8/2015  | Contorni ............ A61K 39/0018 424/197.11 |
| 2015/0273036 | A1 * | 10/2015 | Tarli .................... A61K 39/0016 424/196.1 |
| 2016/0193322 | A1 * | 7/2016  | Steff .................... A61K 39/155 424/186.1 |

FOREIGN PATENT DOCUMENTS

| EP | 0728492 | * | 8/1996 | ............ A61M 5/315 |
| EP | 0728492 | A2 * | 8/1996 | ............ A61M 5/315 |

(Continued)

OTHER PUBLICATIONS

Southern, J, et al., "Immunogenicity and reactogenicity of combined acellular pertussis/tetanus/low dose diphtheria vaccines given as a booster to UK teenagers," Vaccine 23(29): 3829-3835 (2005).

(Continued)

*Primary Examiner* — Albert Navarro
*Assistant Examiner* — Ginny Portner
(74) *Attorney, Agent, or Firm* — Morrison & Foerster LLP

(57) ABSTRACT

A liquid D-T-Pa component is used to reconstitute a lyophilised meningococcal component, thereby producing a combined vaccine.

43 Claims, No Drawings

(56) References Cited

FOREIGN PATENT DOCUMENTS

| WO | 98/19702 | * | 5/1998 | ............. A61K 39/10 |
| --- | --- | --- | --- | --- |
| WO | 98/19702 A1 | | 5/1998 | |
| WO | 99/13906 | * | 3/1999 | ........... A61K 39/295 |
| WO | 02/00249 A2 | | 1/2002 | |
| WO | 02/080965 | * | 10/2002 | ........... A61K 39/295 |
| WO | 02/080965 A2 | | 10/2002 | |
| WO | 03/007985 | * | 1/2003 | ............. A61K 39/02 |
| WO | 2004/039399 | * | 5/2004 | ............. A61K 39/13 |
| WO | 2004/067030 | * | 8/2004 | ........... A61K 39/295 |
| WO | 2004/110480 | * | 12/2004 | ............. A61K 39/00 |
| WO | 2005/089794 | * | 9/2005 | ............. A61K 39/12 |
| WO | 2005/105141 | * | 11/2005 | ........... A61K 39/095 |
| WO | 2006/075170 A1 | | 7/2006 | |
| WO | 2006/097851 A2 | | 9/2006 | |
| WO | 2007/026249 | * | 3/2007 | ............. A61K 30/09 |
| WO | 2007/026249 A2 | | 3/2007 | |
| WO | 2008/020328 | * | 2/2008 | |
| WO | 2008/028956 | * | 3/2008 | ............. A61K 39/13 |
| WO | 2008028956 | * | 3/2008 | ............. A61K 39/13 |
| WO | 2008/081022 A1 | | 7/2008 | |

OTHER PUBLICATIONS

Knuf, M., et al., "Immunogenicity of a single dose of reduced-antigen acellular pertussis vaccine in a non-vaccinated adolescent population," Vaccine 24(12):2043-2048 (2006).

Corbel (1994). "Control testing of combined vaccines: a consideration of potential problems and approaches," Biologicals. 22(4):353-60.

Rappuoli et al. (1996). "European Commission COST/STD Initiative. Report of the expert panel VIII. New vaccines, especially new combined vaccines," Vaccine. 14(7):691-700.

\* cited by examiner

MIXING LYOPHILISED MENINGOCOCCAL VACCINES WITH D-T-PA VACCINES

This patent application is the U.S. National Phase of International Application No. PCT/IB2009/007926, filed 11 Dec. 2009 and published in English, which claims priority from United Kingdom patent application 0822633.4, filed 11Dec. 2008, the teachings of which are incorporated herein in their entirety by reference.

TECHNICAL FIELD

This invention is in the field of formulating combination vaccines for immunising against diphtheria, tetanus, whooping cough and meningococcal meningitis.

BACKGROUND ART

Vaccines containing antigens from more than one pathogenic organism within a single dose are known as "multivalent" or "combination" vaccines e.g. diphtheria, tetanus & pertussis ("DTP") vaccines and measles, mumps & rubella ("MMR") vaccines. Combination vaccines offer patients the advantage of receiving a reduced number of injections, which leads to the clinical advantage of increased compliance (e.g. see chapter 29 of reference 1), particularly for pediatric vaccination. At the same time, however, they present difficulties due to factors including: physical and biochemical incompatibility between antigens and other components; immunological interference; and stability. Some of these difficulties can be addressed by suitable formulation of the vaccine.

DTP vaccines have previously been combined with meningococcal conjugates. For instance, reference 2 prepared a fully-liquid 8-valent D-T-Pw-HBsAg-Hib-MenC-MenW135-MenY vaccine. It also discloses vaccines prepared by mixing aqueous D-T-Pw-HBsAg components with lyophilised mixtures of meningococcal conjugates. A similar liquid/lyophilised formulation is disclosed in reference 3, where a 7-valent combination vaccine was prepared by using a liquid 4-valent D-T-Pw-HBsAg combination vaccine (TRITANRIX HEPB™) to reconstitute a lyophilised Hib-MenA-MenC conjugate component (see also references 29, 30, 76 & 99). Similarly, reference 4 prepared a 7-valent combination vaccine by using a liquid 5-valent D-T-Pa-IPV-HBsAg combination vaccine (INFANRIX PENTA™) to reconstitute a lyophilised MenC-MenY conjugate component. The concentration of antigens and adjuvant in these three documents were, per millilitre:

|  | Ref. 2 | Ref. 3 | Ref. 4 |
|---|---|---|---|
| Diphtheria toxoid | 15 Lf | 15 Lf | 50 Lf |
| Tetanus toxoid | 6.5 Lf | 6.5 Lf | 20 Lf |
| Pertussis | Pw: 30 OU | Pw: 30 OU | Pa: 50 µg PT, 50 µg FHA, 16 µg PRN |
| Al$^{+++}$ | 0.6 mg | 1.26 mg | 1.4 mg |

It is an aim of the invention to provide further and improved formulations for combination vaccines that include diphtheria, tetanus, pertussis and meningococcal antigens. A further aim for some embodiments is to provide formulations that are useful for adolescent immunisation (e.g. boosters).

DISCLOSURE OF THE INVENTION

According to the invention, a liquid component containing D-T-Pa antigens is used to reconstitute a lyophilised meningococcal component. Compared to references 2 to 4, a lower diphtheria toxoid and/or tetanus toxoid content is used, such that the final reconstituted compositions include ≤10 Lf/ml of diphtheria toxoid and/or ≤15 Lf/ml tetanus toxoid. Unlike references 2 to 4, the diphtheria toxoid content will usually be lower than the tetanus toxoid content (measured in Lf units). In some embodiments, a low content of pertussis toxoid (<25 µg/ml) is also used. A low aluminium content may also be used (<0.84 mg/ml, measured as Al$^{+++}$).

By using acellular pertussis antigens ('Pa'), rather than cellular pertussis antigen ('Pw'), the vaccines of the invention can be more easily characterised, more consistent and less reactogenic than the vaccines of references 2 and 3.

By using a lower diphtheria toxoid content than the prior art, vaccines of the invention offer lower reactogenicity and also, in adolescents, address the potential for carrier-induced epitopic suppression, in which excess use of a protein component, either as an immunogen or a conjugate's carrier protein, can result in reduced efficacy (see also the introduction to reference 5). As routine pediatric vaccination now involves administration of various derivatives of diphtheria toxin (diphtheria toxoid is received by children in diphtheria vaccines and as the carrier protein in the MENACTRA™ 4-valent meningococcal conjugate vaccine, and the CRM197 mutant of diphtheria toxin is received as the carrier protein in various conjugate vaccines, including HIBTITER™, PREVENAR™, MENJUGATE™ & MENINGITEC™) then it is useful to reduce the amount of diphtheria toxoid given in vaccines, particularly in adolescent booster vaccines. The lower dosage in the DTPa-containing component also helps to maintain a lower overall diphtheria toxoid dose when a meningococcal conjugate uses diphtheria toxoid or a mutant thereof as a carrier.

By using a lower tetanus toxoid content than the prior art DTPa vaccine of reference 4, vaccines of the invention address the potential for carrier-induced epitopic suppression where pediatric vaccination has involved a tetanus toxoid carrier e.g. from the HIBERIX™ product. The lower dosage in the DTPa-containing component also helps to maintain a lower overall tetanus toxoid dose when a meningococcal conjugate uses tetanus toxoid as a carrier.

Reducing pertussis toxoid content [6] and aluminium dose [7] has also been reported to be advantageous in adolescents.

Thus the invention provides a kit comprising: (i) an aqueous component, comprising a mixture of diphtheria toxoid, tetanus toxoid and acellular pertussis antigens, in which the concentration of diphtheria toxoid is ≤10 Lf/ml; and (ii) a lyophilised component, comprising a conjugate of a *Neisseria meningitidis* capsular saccharide. For administration to a patient, the aqueous and lyophilised components are combined, to give a combined liquid vaccine that is suitable for injection.

The invention also provides a method for preparing a combined vaccine, comprising the step of combining: (i) an aqueous component, comprising a mixture of diphtheria toxoid, tetanus toxoid and acellular pertussis antigens, in which the concentration of diphtheria toxoid is ≤10 Lf/ml; and (ii) a lyophilised component, comprising a conjugate of a *Neisseria meningitidis* capsular saccharide.

The invention also provides a combined vaccine comprising diphtheria toxoid, tetanus toxoid, acellular pertussis antigens and a conjugate of a *Neisseria meningitidis* capsular saccharide, wherein the concentration of diphtheria toxoid is ≤10 Lf/ml and the vaccine is prepared by combining a lyophilised *N. meningitidis* conjugate with an aqueous mixture of diphtheria toxoid, tetanus toxoid and acellular pertussis antigens. The vaccine may include one or more lyophilisation stabiliser(s).

The invention also provides a kit comprising: (i) an aqueous component, comprising a mixture of diphtheria toxoid, tetanus toxoid and acellular pertussis antigens, in which the concentration of tetanus toxoid is ≤15 Lf/ml; and (ii) a lyophilised component, comprising a conjugate of a *Neisseria meningitidis* capsular saccharide. For administration to a patient, the aqueous and lyophilised components are combined, to give a combined liquid vaccine that is suitable for injection.

The invention also provides a method for preparing a combined vaccine, comprising the step of combining: (i) an aqueous component, comprising a mixture of diphtheria toxoid, tetanus toxoid and acellular pertussis antigens, in which the concentration of tetanus toxoid is ≤15 Lf/ml; and (ii) a lyophilised component, comprising a conjugate of a *Neisseria meningitidis* capsular saccharide.

The invention also provides a combined vaccine comprising diphtheria toxoid, tetanus toxoid, acellular pertussis antigens and a conjugate of a *Neisseria meningitidis* capsular saccharide, wherein the concentration of tetanus toxoid is ≤15 Lf/ml and the vaccine is prepared by combining a lyophilised *N. meningitidis* conjugate with an aqueous mixture of diphtheria toxoid, tetanus toxoid and acellular pertussis antigens. The vaccine may include one or more lyophilisation stabiliser(s)

The invention also provides a kit comprising: (i) an aqueous component, comprising a mixture of diphtheria toxoid, tetanus toxoid and acellular pertussis antigens, in which the concentration of diphtheria toxoid is ≤10 Lf/ml and the concentration of tetanus toxoid is ≤15 Lf/ml; and (ii) a lyophilised component, comprising a conjugate of a *Neisseria meningitidis* capsular saccharide. For administration to a patient, the aqueous and lyophilised components are combined, to give a combined liquid vaccine that is suitable for injection.

The invention also provides a method for preparing a combined vaccine, comprising the step of combining: (i) an aqueous component, comprising a mixture of diphtheria toxoid, tetanus toxoid and acellular pertussis antigens, in which the concentration of diphtheria toxoid is ≤10 Lf/ml and the concentration of tetanus toxoid is ≤15 Lf/ml; and (ii) a lyophilised component, comprising a conjugate of a *Neisseria meningitidis* capsular saccharide.

The invention also provides a combined vaccine comprising diphtheria toxoid, tetanus toxoid, acellular pertussis antigens and a conjugate of a *Neisseria meningitidis* capsular saccharide, wherein the concentration of diphtheria toxoid is ≤10 Lf/ml and the concentration of tetanus toxoid is ≤15 Lf/ml, and the vaccine is prepared by combining a lyophilised *N. meningitidis* conjugate with an aqueous mixture of diphtheria toxoid, tetanus toxoid and acellular pertussis antigens. The vaccine may include one or more lyophilisation stabiliser(s)

The invention also provides a kit comprising: (i) an aqueous component, comprising a mixture of diphtheria toxoid, tetanus toxoid and acellular pertussis antigens, in which the concentration of diphtheria toxoid is lower than the concentration of tetanus toxoid (both measured in Lf units); and (ii) a lyophilised component, comprising a conjugate of a *Neisseria meningitidis* capsular saccharide. The diphtheria toxoid concentration is ideally ≤10 Lf/ml and the tetanus toxoid content is ideally ≤15 Lf/ml. For administration to a patient, the aqueous and lyophilised components are combined, to give a combined liquid vaccine that is suitable for injection.

The invention also provides a method for preparing a combined vaccine, comprising the step of combining: (i) an aqueous component, comprising a mixture of diphtheria toxoid, tetanus toxoid and acellular pertussis antigens, in which the concentration of diphtheria toxoid is lower than the concentration of tetanus toxoid (both measured in Lf units); and (ii) a lyophilised component, comprising a conjugate of a *Neisseria meningitidis* capsular saccharide. The diphtheria toxoid concentration is ideally ≤10 Lf/ml and the tetanus toxoid content is ideally ≤15 Lf/ml.

The invention also provides a combined vaccine comprising diphtheria toxoid, tetanus toxoid, acellular pertussis antigens and a conjugate of a *Neisseria meningitidis* capsular saccharide, wherein the concentration of diphtheria toxoid is lower than the concentration of tetanus toxoid (both measured in Lf units) and the vaccine is prepared by combining a lyophilised *N. meningitidis* conjugate with an aqueous mixture of diphtheria toxoid, tetanus toxoid and acellular pertussis antigens. The diphtheria toxoid concentration is ideally ≤10 Lf/ml and the tetanus toxoid content is ideally ≤15 Lf/ml. The vaccine may include one or more lyophilisation stabiliser(s)

The invention also provides a kit comprising: (i) an aqueous component, comprising a mixture of diphtheria toxoid, tetanus toxoid and acellular pertussis antigens; and (ii) a lyophilised component, comprising conjugate of capsular saccharide from *Neisseria meningitidis* serogroup A and/or *Neisseria meningitidis* serogroup W135. For administration to a patient, the aqueous and lyophilised components are combined, to give a combined liquid vaccine that is suitable for injection.

The invention also provides a method for preparing a combined vaccine, comprising the step of combining: (i) an aqueous component, comprising a mixture of diphtheria toxoid, tetanus toxoid and acellular pertussis antigens; and (ii) a lyophilised component, comprising conjugate of capsular saccharide from *Neisseria meningitidis* serogroup A and/or *Neisseria meningitidis* serogroup W135.

The invention also provides a combined vaccine comprising (i) diphtheria toxoid, tetanus toxoid, acellular pertussis antigens, and (ii) a conjugate of capsular saccharide from *Neisseria meningitidis* serogroup A and/or *Neisseria meningitidis* serogroup W135; wherein the vaccine is prepared by combining one or more lyophilised *N. meningitidis* conjugate(s) with an aqueous mixture of diphtheria toxoid, tetanus toxoid and acellular pertussis antigens. The vaccine may include one or more lyophilisation stabiliser(s).

In all of these embodiments the aqueous component will typically include an adjuvant, such as one or more aluminium salts. In such components the aluminium content is usually less than 1.7 mg/ml, and can be less than 0.84 mg/ml, as explained in more detail below. The lyophilised component may also include an adjuvant, or may instead be unadjuvanted.

In all of these embodiments the concentration of pertussis toxoid in the aqueous component will typically be less than 25 µg/ml.

The Liquid Component

Kits and methods of the invention involve the use of an aqueous antigenic component that includes a mixture of diphtheria toxoid, tetanus toxoid and acellular pertussis antigens. The concentration of diphtheria toxoid in the aqueous component is usually ≤10 Lf/ml e.g. ≤5 Lf in a 0.5 ml dose volume. The concentration of tetanus toxoid in the aqueous component is usually ≤15 Lf/ml e.g. ≤7.5 Lf in a 0.5 ml volume. The concentration of diphtheria toxoid is typically lower than the concentration of tetanus toxoid, both concentrations being measured in Lf units.

Diphtheria toxin is produced by *Corynebacterium diphtheriae*, the cause of diphtheria. The toxin can be treated (e.g. using formalin or formaldehyde) to remove toxicity while retaining the ability to induce specific anti-toxin antibodies after injection. These diphtheria toxoids are used in diphtheria vaccines, and are disclosed in more detail in chapter 13 of reference 1. Preferred diphtheria toxoids are those prepared by formaldehyde treatment. The diphtheria toxoid can be obtained by growing *C. diphtheriae* in growth medium (e.g. Fenton medium, or Linggoud & Fenton medium), which may be supplemented with bovine extract, followed by formaldehyde treatment, ultrafiltration and precipitation. The toxoided material may then be treated by a process comprising sterile filtration and/or dialysis.

Tetanus toxin is produced by *Clostridium tetani*, the cause of tetanus. As the diphtheria, the tetanus toxin can be treated to give a protective toxoid. The toxoids are used in tetanus vaccines, and are disclosed in more detail in chapter 27 of reference 1. Preferred tetanus toxoids are those prepared by formaldehyde treatment. The tetanus toxoid can be obtained by growing *C. tetani* in growth medium (e.g. a Latham medium derived from bovine casein), followed by formaldehyde treatment, ultrafiltration and precipitation. The material may then be treated by a process comprising sterile filtration and/or dialysis.

*Bordetella pertussis* causes whooping cough. Pertussis antigens in commercial vaccines are either cellular (whole cell, in the form of inactivated *B. pertussis* cells; 'Pw') or acellular (specific purified *B. pertussis* antigens; 'Pa'). The invention uses acellular pertussis antigens, which usually include one, two or (preferably) three of the following purified antigens: (1) inactivated pertussis toxin (pertussis toxoid, or 'PT'); (2) filamentous hemagglutinin ('FHA'); (3) pertactin (also known as the '69 kiloDalton outer membrane protein' or 'PRN'). These three antigens can be prepared by isolation from *B. pertussis* culture grown in modified Stainer-Scholte liquid medium. Pertussis toxin and FHA can be isolated from the fermentation broth (e.g. by adsorption on hydroxyapatite gel), whereas pertactin can be extracted from the cells by heat treatment and flocculation (e.g. using barium chloride). The antigens can be purified in successive chromatographic and/or precipitation steps. Pertussis toxin and FHA can be purified by, for example, hydrophobic chromatography, affinity chromatography and size exclusion chromatography. Pertactin can be purified by, for example, ion exchange chromatography, hydrophobic chromatography and size exclusion chromatography. FHA and pertactin may be treated with formaldehyde prior to use according to the invention. Pertussis toxin may be inactivated (detoxified), to give PT, by treatment with formaldehyde and/or glutaraldehyde; as an alternative to this chemical detoxification procedure the PT may be a mutant toxin in which enzymatic activity has been reduced by mutagenesis [8] (e.g. the 91K/129G mutant [9]), but detoxification by chemical treatment is more usual. As well as PT, FHA and pertactin, it is also possible to include fimbriae (e.g. agglutinogens 2 and 3) in an acellular pertussis antigen component.

The concentration of diphtheria toxoid in the aqueous component is ideally ≤10 Lf/ml (i.e. ≤5 Lf in a 0.5 ml dose volume). Within this range, a typical diphtheria toxoid concentration is between 2 Lf/ml and 7 Lf/ml or between 3 Lf/ml and 6 Lf/ml. Preferred concentrations are about 4 Lf/ml or about 5 Lf/ml. The 'Lf' unit ("flocculating units" or the "limes flocculating dose") is defined as the amount of toxoid which, when mixed with one International Unit of antitoxin, produces an optimally flocculating mixture [10]. For measuring these quantities the NIBSC, for example, supplies 'Diphtheria Toxoid, Plain' [11], which contains 300 Lf per ampoule, and also supplies 'The 1st International Reference Reagent For Diphtheria Toxoid For Flocculation Test' [12] which contains 900 Lf per ampoule.

The concentration of tetanus toxoid in the aqueous component may be in the range of 1-30 Lf/ml. Within this range, a typical tetanus toxoid concentration is between 5 Lf/ml and 25 Lf/ml or between 8 Lf/ml and 15 Lf/ml. Ideally the content is ≤15 Lf/ml, and preferably is about 10 Lf/ml. For measuring Lf units the NIBSC, for example, supplies 'The 1st International Reference Reagent for Tetanus Toxoid For Flocculation Test' [13] which contains 1000 Lf per ampoule.

The diphtheria toxoid content will usually be lower than the tetanus toxoid content, measured in Lf units e.g. a D:T ratio of between 1:2 and 1:4 e.g. about 1:2, about 1:2.5 or about 1:3.

Where the aqueous component includes PT in an acellular pertussis antigen, its concentration may be in the range of 1 μg/ml to 100 μg/ml or between 2 μg/ml and 55 μg/ml. A concentration of below 25 μg/ml or below 18 μg/ml is particularly useful e.g. about 5 μg/ml, about 10 μg/ml, about 15 μg/ml, about 16 μg/ml.

Where the aqueous component includes FHA in an acellular pertussis antigen, its concentration may be in the range of 1 μg/ml to 100 μg/ml or between 5 μg/ml and 55 μg/ml e.g. about 5 μg/ml, about 10 μg/ml, about 15 μg/ml, about 16 μg/ml.

Where the aqueous component includes pertactin in an acellular pertussis antigen, its concentration may be in the range of 2 μg/ml to 20 μg/ml or between 4 μg/ml and 10 μg/ml e.g. about 5 μg/ml or about 6 μg/ml.

Where the aqueous component includes each of PT, FHA and pertactin, their weight ratios can vary, but may be e.g. about 16:16:5 or about 5:10:6 (PT:FHA:PRN).

Where the aqueous component includes fimbriae types 2 and 3 in an acellular pertussis antigen, their combined concentration may be in the range of 2 μg/ml to 20 μg/ml or between 5 μg/ml and 15 μg/ml e.g. about 10 μg/ml.

A useful acellular pertussis component has 10 μg/ml PT (preferably 9K/129G mutant), 5 μg/ml FHA and 5 μg/ml PRN. Another useful acellular pertussis component has 5 μg/ml PT (preferably 9K/129G mutant), 2.5 μg/ml FHA and 2.5 μg/ml PRN.

In addition to the D, T and Pa antigens, the aqueous component can include an adjuvant. The adjuvant may comprise one or more aluminium salts, such as an aluminium hydroxide and/or an aluminium phosphate. The aluminium content (measured as $Al^{+++}$) is usually less than 1.7 mg/ml, and can be less than 0.84 mg/ml e.g. between 0.4-0.8 mg/ml, between 0.5-0.7 mg/ml, about 0.8 mg/ml, about 0.6 mg/ml, about 0.66 mg/ml, about 0.27 mg/ml, etc.

Where aluminium salt(s) are present in the aqueous component, the D, T and/or Pa antigens may be adsorbed to them. For instance, all of the D, T and Pa antigens may be individually adsorbed to an aluminium hydroxide adjuvant and then mixed to prepare the aqueous component. As an alternative, all of the D, T and Pa antigens may be individually adsorbed to an aluminium phosphate adjuvant and then mixed. Sequential adsorption can also be used, as can adsorption to mixtures of different aluminium salts. Antigens are typically fully adsorbed, although for tetanus toxoid full adsorption may sometimes be avoided e.g. adsorption of between 0-10% of the total tetanus toxoid can be used.

A useful adjuvanted acellular pertussis component has 10 µg/ml PT (preferably 9K/129G mutant), 5 µg/ml FHA, 5 µg/ml PRN, 2 mg/ml aluminium hydroxide, 9 mg/ml sodium chloride and 0.1 mg/ml thimerosal. Another useful adjuvanted acellular pertussis component has 5 µg/ml PT (preferably 9K/129G mutant), 2.5 µg/ml FHA, 2.5 µg/ml PRN, 2 mg/ml aluminium hydroxide, 9 mg/ml sodium chloride and 0.1 mg/ml thimerosal.

Where antigens are adsorbed, a composition may be a suspension with a cloudy appearance, meaning that microbial contamination may not be readily visible. Thus an aqueous component may contain a preservative, particularly when the vaccine is packaged in multidose containers. It is preferred, however, not to use mercurial preservatives (e.g. thimerosal), but if mercury cannot be avoided then compositions should contain <25 ng/ml mercury. Mercury-free compositions are preferred, and a useful non-mercurial preservative is 2-phenoxyethanol (2-PE). 2-PE levels of less than 10 mg/ml are typical e.g. between 4-7 mg/ml e.g. about 5 mg/ml, or about 6.6 mg/ml. In some embodiments, however, the aqueous component can be preservative-free.

The aqueous component will usually be free from meningococcal capsular saccharide(s).

Sixteen specific embodiments of the aqueous component include: (a) a preservative-free mixture comprising 2.5 Lf diphtheria toxoid, 5 Lf tetanus toxoid, 2.5 µg pertactin, 8 µg FHA and 8 µg pertussis toxoid, usually in a 0.5 ml volume; (b) a preservative-free mixture comprising 2.5 Lf diphtheria toxoid, 5 Lf tetanus toxoid, 2.5 µg pertactin, 8 µg FHA, 8 µg pertussis toxoid, 4.5 mg sodium chloride and an aluminium hydroxide adjuvant with <0.4 mg $Al^{+++}$ e.g. 0.3 mg $Al^{+++}$; (c) a mixture comprising 2.5 Lf diphtheria toxoid, 5 Lf tetanus toxoid, 2.5 µg pertactin, 8 µg FHA, 8 µg pertussis toxoid, 4.5 mg sodium chloride, 2.5 mg 2-phenoxyethanol and an aluminium hydroxide adjuvant with <0.6 mg $Al^{+++}$; (d) a preservative-free mixture comprising 5 Lf/ml diphtheria toxoid, 10 Lf/ml tetanus toxoid, 5 µg/ml pertactin, 16 µg/ml FHA and 16 µg/ml pertussis toxoid; (e) a preservative-free mixture comprising 5 Lf/ml diphtheria toxoid, 10 Lf/ml tetanus toxoid, 5 µg/ml pertactin, 16 µg/ml FHA, 16 µg/ml pertussis toxoid, 9 mg/ml sodium chloride and an aluminium hydroxide adjuvant with <0.8 mg/ml $Al^{+++}$ e.g. 0.6 mg/ml $Al^{+++}$; (f) a mixture comprising 5 Lf/ml diphtheria toxoid, 10 Lf/ml tetanus toxoid, 5 µg/ml pertactin, 16 µg/ml FHA, 16 µg/ml pertussis toxoid, 9 mg/ml sodium chloride, 5 µg/ml 2-phenoxyethanol and an aluminium hydroxide adjuvant with <1.1 mg/ml $Al^{+++}$; (g) to (i) are embodiments (a) to (c) but also including 40 DU type 1 poliovirus, 8 DU type 2 poliovirus, and 32 DU of type 3 poliovirus; (j) to (l) are embodiments (d) to (f) but also including 80 DU/ml type 1 poliovirus, 16 DU/ml type 2 poliovirus, and 64 DU/ml type 3 poliovirus; (m) a mixture comprising 2 Lf diphtheria toxoid, 5 Lf tetanus toxoid, 3 µg pertactin, FHA, 2.5 µg pertussis toxoid, 5 µg pertussis fimbriae types 2 & 3, 3.3 mg 2-phenoxyethanol and an aluminium phosphate adjuvant with <0.35 mg $Al^{+++}$; (n) a preservative-free mixture comprising 2 Lf diphtheria toxoid, 5 Lf tetanus toxoid, 3 µg pertactin, 5 µg FHA, 2.5 µg pertussis toxoid, 5 µg pertussis fimbriae types 2 & 3, and an aluminium phosphate adjuvant with ≤0.35 mg $Al^{+++}$; (o) a mixture comprising 4 Lf/ml diphtheria toxoid, 10 Lf/ml tetanus toxoid, 6 µg/ml pertactin, 10 µg/ml FHA, 5 µg/ml pertussis toxoid, 10 µg/ml pertussis fimbriae types 2 & 3, 6.6 mg/ml 2-phenoxyethanol and an aluminium phosphate adjuvant with ≤0.7 mg/ml $Al^{+++}$; (p) a preservative-free mixture comprising 4 Lf/ml diphtheria toxoid, 10 Lf/ml tetanus toxoid, 6 µg/ml pertactin, 10 µg/ml FHA, 5 µg/ml pertussis toxoid, 10 µg/ml pertussis fimbriae types 2 & 3, and an aluminium phosphate adjuvant with ≤0.7 mg $Al^{+++}$. Seven further embodiments of the aqueous component comprise: (a) 20 Lf/ml tetanus toxoid, 50 Lf/ml diphtheria toxoid, 10 µg/ml PT (preferably 9K/129G mutant), 5 µg/ml FHA and 5 µg/ml PRN; (b) 10 Lf/ml tetanus toxoid, 25 Lf/ml diphtheria toxoid, 5 µg/ml PT (preferably 9K/129G mutant), 2.5 µg/ml FHA and 2.5 µm/ml PRN; (c) 10 Lf/ml tetanus toxoid, 30 Lf/ml diphtheria toxoid, 5 µg/ml PT (preferably 9K/129G mutant), 2.5 µg/ml FHA and 2.5 µg/ml PRN; (d) 20 Lf/ml tetanus toxoid, 50 Lf/ml diphtheria toxoid, 5 µg/ml PT (preferably 9K/129G mutant), 2.5 µm/ml FHA and 2.5 µg/ml PRN; (e) 10 Lf/ml tetanus toxoid, 5 Lf/ml diphtheria toxoid, 10 µg/ml PT (preferably 9K/129G mutant), 5 µg/ml FHA and 5 µg/ml PRN; (f) 10 Lf/ml tetanus toxoid, 4 Lf/ml diphtheria toxoid, 5 µg/ml PT (preferably 9K/129G mutant), 2.5 µg/ml FHA and 2.5 µg/ml PRN; and (g) between 5-15 Lf/ml tetanus toxoid, between 2-8 Lf/ml diphtheria toxoid, between 1-20 µg/ml PT preferably as the 9K/129G mutant, between 1-20 µg/ml FHA, and 1-20 µg/ml PRN.

The Lyophilised (Freeze-Dried) Component

Kits and methods of the invention use a lyophilised antigenic component that includes a conjugate of a meningococcal capsular saccharide. Administration of the meningococcal conjugate preferably results in a bactericidal antibody response, with an increase in serum bactericidal assay (SBA) titre for the relevant serogroup of at least 4-fold, and preferably at least 8-fold, measured with human complement [14]. If rabbit complement is used to measure SBA titres then the titre increase is preferably at least 128-fold.

Conjugated monovalent vaccines against serogroup C have been approved for human use, and include MENJUGATE™ [15], MENINGITEC™ and NEISVAC-C™. Mixtures of conjugates from serogroups A+C are known [16,17] and mixtures of conjugates from serogroups A+C+W135+Y have been reported [18-21] and were approved in 2005 as the aqueous MENACTRA™ product. The lyophilised component used with the invention may include one or more meningococcal conjugates. Including 2, 3, or 4 of serogroups A, C, W135 and Y is preferred e.g. A+C, A+W135, A+Y, C+W135, C+Y, W135+Y, A+C+W135, A+C+Y, A+W135+Y, A+C+W135+Y, etc. Components including saccharides from all four of serogroups A, C, W135 and Y are preferred.

Where conjugates from more than one serogroup are included then, in some embodiments, they may be present at substantially equal masses e.g. the mass of each serogroup's saccharide is within ±5% of each other. In other embodiments, however, the mass of saccharide from one serogroup may differ from the mass of saccharide in another serogroup e.g. one serogroup may have a dose 2× that of another serogroup. A typical quantity of saccharide per serogroup is between 1 µg and 20 µg e.g. between 2 and 10 µg. For an individual serogroup the mass of saccharide per vaccine dose (e.g. per final 0.5 ml volume) may be, for example, about 2.5 µg, about 4 µg, about 5 µg or about 10 µg.

For compositions including saccharides from serogroups A and C, examples of suitable A:C mass ratios are 1:1 and 2:1. For compositions including saccharides from serogroups C and Y, examples of suitable C:Y mass ratios are 1:1, 1:2 and 2:1. For compositions including saccharides from serogroups C, W135 and Y, examples of suitable C:W135:Y mass ratios are 1:1:1, 2:1:1, 2:2:1, 2:1:2, 1:2:2, 1:2:1 and 1:1:2. For compositions including saccharides from serogroups A, C, W135 and Y, examples of suitable A:C:W135:Y mass ratios are 1:1:1:1, 2:1:1:1, 1:4:1:1, 1:2:1:1 & 2:2:1:1.

The capsular saccharide of serogroup A meningococcus is a homopolymer of (α1 →6)-linked N-acetyl-D-mannosamine-1-phosphate, with partial O-acetylation in the C3 and C4 positions. Acetylation at the C-3 position can be 70-95%. Conditions used to purify the saccharide can result in de-O-acetylation (e.g. under basic conditions), but it is useful to retain OAc at this C-3 position. In some embodiments, at least 50% (e.g. at least 60%, 70%, 80%, 90%, 95% or more) of the mannosamine residues in a serogroup A saccharides are O-acetylated at the C-3 position. Acetyl groups can be replaced with blocking groups to prevent hydrolysis [22], and such modified saccharides are still serogroup A saccharides within the meaning of the invention.

The serogroup C capsular saccharide is a homopolymer of (α2→9)-linked sialic acid (N-acetyl neuraminic acid, or 'NeuNAc'). The saccharide structure is written as →9)-Neu p NAc 7/8 OAc-(α2→. Most serogroup C strains have O-acetyl groups at C-7 and/or C-8 of the sialic acid residues, but about 15% of clinical isolates lack these O-acetyl groups [23,24]. The presence or absence of OAc groups generates unique epitopes, and the specificity of antibody binding to the saccharide may affect its bactericidal activity against O-acetylated (OAc−) and de-O-acetylated (OAc+) strains [25-27]. Serogroup C saccharides used with the invention may be prepared from either OAc+ or OAc− strains. Licensed MenC conjugate vaccines include both OAc− (NEISVAC-C™) and OAc+ (MENJUGATE™& MENINGITEC™) saccharides. In some embodiments, strains for production of serogroup C conjugates are OAc+strains, e.g. of serotype 16, serosubtype P1.7a,1, etc. Thus C:16:P1.7a,1 OAc+strains may be used. OAc+ strains in serosubtype P1.1 are also useful, such as the C11 strain.

The serogroup W135 saccharide is a polymer of sialic acid-galactose disaccharide units. Like the serogroup C saccharide, it has variable O-acetylation, but at sialic acid 7 and 9 positions [28]. The structure is written as: →4)-D-Neup5Ac(7/9OAc)-α-(2→6)-D-Gal-α-(1→. The serogroup W135 saccharides used according to the invention may have the same degree of O-acetylation as seen in native serogroup W135 capsular saccharides, or they may be partially or totally de-O-acetylated at one or more positions of the saccharide ring, or they may be hyper-O-acetylated relative to the native capsular saccharides. In some embodiments, no more than 50% (e.g. at most 40%, 30%, 20%, or 10%; for example, between 40% and 45%) of the sialic acid residues in a serogroup W135 saccharide are O-acetylated at the C-7 and/or C-9 position(s).

The serogroup Y saccharide is similar to the serogroup W135 saccharide, except that the disaccharide repeating unit includes glucose instead of galactose. Like serogroup W135, it has variable O-acetylation at sialic acid 7 and 9 positions [28]. The serogroup Y structure is written as: →4)-D-Neup5Ac(7/9OAc)-α-(2→6)-D-Glc-α-(1→. The serogroup Y saccharides used according to the invention may have the same degree of O-acetylation as seen in native serogroup Y capsular saccharides, or they may be partially or totally de-O-acetylated at one or more positions of the saccharide ring, or they may be hyper-O-acetylated relative to the native capsular saccharides. In some embodiments, no more than 50% (e.g. at most 40%, 30%, 20%, or 10%; for example, between 30% and 40%) of the sialic acid residues in a serogroup Y saccharide are O-acetylated at the C-7 and/or C-9 position(s).

The saccharide moieties in conjugates may comprise full-length saccharides as prepared from meningococci, and/or may comprise fragments of full-length saccharides i.e. the saccharides may be shorter than the native capsular saccharides seen in bacteria. The saccharides may thus be depolymerised, with depolymerisation occurring during or after saccharide purification but before conjugation. Depolymerisation reduces the chain length of the saccharides. One depolymerisation method involves the use of hydrogen peroxide [18]. Hydrogen peroxide is added to a saccharide (e.g. to give a final $H_2O_2$ concentration of 1%), and the mixture is then incubated (e.g. at about 55° C.) until a desired chain length reduction has been achieved. Another depolymerisation method involves acid hydrolysis [19]. Other depolymerisation methods are known in the art. The saccharides used to prepare conjugates for use according to the invention may be obtainable by any of these depolymerisation methods. Depolymerisation can be used in order to provide an optimum chain length for immunogenicity and/or to reduce chain length for physical manageability of the saccharides. In some embodiments, saccharides have the following range of average degrees of polymerisation (Dp): A=10-20; C=12-22; W135=15-25; Y=15-25. In terms of molecular weight, rather than Dp, useful ranges are, for all serogroups: ≤100 kDa; 5 kDa-75 kDa; 7 kDa-50 kDa; 8 kDa-35 kDa; 12 kDa-25 kDa; 15 kDa-22 kDa.

The saccharides used according to the invention may be O-acetylated with the same O-acetylation pattern as seen in native capsular saccharides, or they may be partially or totally de-O-acetylated at one or more positions of the saccharide rings, or they may be hyper-O-acetylated relative to the native capsular saccharides.

Useful carrier proteins (see below) include CRM197, diphtheria toxoid and/or tetanus toxoid. Where the lyophilised component includes conjugates from more than one meningococcal serogroup then the various conjugates may use different carrier proteins (e.g. one serogroup on CRM197, another on tetanus toxoid) or they may use the same carrier protein (e.g. saccharides from two serogroups separately conjugated to CRM197 and then combined).

Suitable meningococcal conjugates can be made by the methods disclosed in, for example, any of references 18, 19, 29, 30, 31, 32, 33, 75, 76, 97 and/or 99, or by any other suitable method.

A preferred lyophilised component includes the meningococcal conjugates from serogroups A, C, W135 and Y as described in references 33 and 34 (the full contents of both of which are incorporated by reference herein).

Another useful lyophilised component is unadjuvanted and includes 5 μg of capsular saccharide for each of serogroups A, C, W135 and Y, with each serogroup's saccharide being separately conjugated to a tetanus toxoid carrier, as described in reference 35 (the full contents of which are incorporated by reference herein.

As an alternative to purifying saccharides from bacteria, saccharides may be prepared by chemical synthesis, in full or in part [36,37].

For stability reasons, a lyophilised component may include a stabiliser such as lactose, sucrose, trehalose or mannitol, as well as mixtures thereof e.g. lactose/sucrose mixtures, sucrose/mannitol mixtures, etc. Using a sucrose/mannitol mixture can speed up the drying process.

A lyophilised component may also include sodium chloride.

Soluble components in the lyophilised material will be retained in the composition after reconstitution. Thus the final combined vaccine may contain one or more such stabilisers (e.g. may include lactose and/or sucrose) and may contain sodium chloride.

The lyophilised component may or may not include an adjuvant, such as an aluminium salt.

The lyophilised component will usually be free from pertussis antigen(s). It will also usually be free from diphtheria toxoid and tetanus toxoid, except for any toxoid(s) that have been used as carrier proteins during conjugation of the meningococcal conjugate(s).

Eleven specific embodiments of the lyophilised component include: (a) a mixture comprising saccharides from serogroups A and C, each separately conjugated to tetanus toxoid, to give a final vaccine dose of 2.5 µg for each serogroup; (b) a mixture comprising saccharides from serogroups A and C, each separately conjugated to tetanus toxoid, to give a final vaccine dose of 5 µg for each serogroup; (c) a mixture comprising saccharides from serogroups C and Y, each separately conjugated to tetanus toxoid, to give a final vaccine dose of 5 µg for each serogroup; (d) a mixture comprising saccharides from serogroups C and Y, each separately conjugated to tetanus toxoid, to give a final vaccine dose of 10 µg for each serogroup; (e) a mixture comprising saccharides from serogroups A, C, W135 and Y, each separately conjugated to CRM197, to give a final vaccine dose of 10 µg for serogroup A and 5 µg for serogroups C, W135 & Y; (f) a mixture comprising saccharides from serogroups A, C, W135 and Y, each separately conjugated to diphtheria toxoid, to give a final vaccine dose of 5 µg for each serogroup; (g) a mixture comprising saccharides from serogroups A, C, W135 and Y, each separately conjugated to tetanus toxoid, to give a final vaccine dose of 2.5 µg for each serogroup; (h) a mixture comprising saccharides from serogroups A, C, W135 and Y, each separately conjugated to tetanus toxoid, to give a final vaccine dose of 5 µg for each serogroup; (i) a mixture comprising saccharides from serogroups A, C, W135 and Y, each separately conjugated to tetanus toxoid, to give a final vaccine dose of 2.5 µg for serogroups A, W135 and Y and 10 µg for serogroup C; (j) a mixture comprising saccharides from serogroups A, C, W135 and Y, each separately conjugated to tetanus toxoid, to give a final vaccine dose of 2.5 µg for serogroups A, W135 and Y and 5 µg for serogroup C; and (k) a mixture comprising saccharides from serogroups A, C, W135 and Y, each separately conjugated to tetanus toxoid, to give a final vaccine dose of 2.5 µg for serogroups W135 and Y and 5 µg for serogroups A and C.

Packaging Compositions of the Invention

The wet and dry components used with the invention must be kept separate from each other prior to use. Thus they are packaged separately in the form of a kit. The kit can take various forms.

In some embodiments, the two components are packaged into separate containers. In other embodiments, the two components are packaged into separate chambers of a single container e.g. into separate containers of a multi-chamber syringe. A dual-chamber syringe allows two individual compositions to be kept separately during storage, but to be mixed as the syringe plunger is activated.

Lyophilised material will usually be presented in a sealed vial. The vial will have an opening (e.g. a rubber seal, a breakable neck, etc.) that can maintain sterility while permitting removal of its contents and/or introduction of aqueous material for reconstitution. Vials can be made of various materials e.g. of a glass, of a plastic, etc.

Aqueous material may also be presented in a vial, but as an alternative may be presented in e.g. a syringe. Again, the container will be able to maintain sterility while permitting removal of its contents. A syringe may be applied with or without a needle attached to it; in the latter case, a separate needle may be packaged with the syringe for assembly and use, and the syringe will generally have a tip cap to seal the tip prior to attachment of a needle. Safety needles are preferred. 1-inch 23-gauge, 1-inch 25-gauge and ⅝-inch 25-gauge needles are typical. The plunger in a syringe may have a stopper to prevent the plunger from being accidentally removed during aspiration. Syringes can be made of various materials e.g. of a glass, of a plastic, etc.

A vial can have a cap (e.g. a Luer lock) adapted such that a syringe can be inserted into the cap, the contents of the syringe can be expelled into the vial (to reconstitute lyophilised material therein), and the contents of the vial can be removed back into the syringe. After removal of the syringe from the vial, a needle can then be attached and the composition can be administered to a patient. The cap may be located inside a seal or cover, such that the seal or cover has to be removed before the cap can be accessed.

Where material is packaged in a container, the container will usually be sterilized before the material is added to it.

Where a glass container (e.g. a syringe or a vial) is used, then it can usefully be made from a borosilicate glass rather than from a soda lime glass.

Reconstitution

Prior to administration to a patient, the invention involves reconstitution of a lyophilised antigenic component (containing at least one meningococcal conjugate) with an aqueous component (containing at least D-T-Pa antigens). Reconstitution can involve various steps.

If the components are present in a multi-chamber syringe then actuation of the syringe will combine the aqueous and dried materials. Where the components are present in separate containers, different mixing processes can be used. In some embodiments, aqueous material in a vial can be extracted into a syringe (e.g. via a needle), or may already be present in a syringe. The aqueous material can then be transferred from the syringe into a vial containing the lyophilised material (e.g. via a needle, which may be the same as or different from a needle previously used to extract aqueous material from a vial). The lyophilised material is thereby reconstituted and can be withdrawn (e.g. via a needle, again being the same as or different from a previously-used needle) into a syringe (e.g. the same as or different from a previously-used syringe), from which it can be injected into a patient (e.g. via a needle, again being the same as or different from a previously-used needle).

Once the lyophilised material and aqueous material have been combined and are present in a delivery device (typically a syringe) then the composition can be administered to a patient. Reconstitution will typically take place immediately prior to administration to a patient e.g. no more than 30 minutes prior to injection.

After reconstitution, a composition for administration to a patient will include diphtheria toxoid, tetanus toxoid, acellular pertussis antigen(s) and meningococcal conjugate(s). The D, T and Pa antigens originate from original aqueous material and a meningococcal conjugate originates from original lyophilised material. The original aqueous material may also include a meningococcal conjugate e.g. the lyophilised material may include conjugates from serogroups A and W135, and the aqueous material includes a conjugate from serogroup C. Usually, however, the aqueous component will be free from meningococcal capsular saccharides.

Methods of Treatment and Administration of the Vaccine

The invention involves the co-administration of D, T, Pa and meningococcal conjugates in the form of a combination vaccine. The reconstituted compositions are suitable for administration to human patients, and the invention provides a method of raising an immune response in a patient, comprising the step of administering to the patient a composition of the invention.

The invention also provides a composition of the invention for use in medicine.

The invention also provides the use of (i) an aqueous component, as described above; and (ii) a lyophilised component, as described above, in the manufacture of a medicament for administration to a patient.

The invention also provides a combination of (i) an aqueous component, as described above; and (ii) a lyophilised component, as described above, for use in immunisation.

Reconstituted compositions of the invention are preferably vaccines, for use in the reduction or prevention of diphtheria, tetanus, whooping cough and meningitis. The vaccines may be used as booster vaccines in patients who have previously been immunised against one or more of diphtheria, tetanus, whooping cough and/or meningococcal meningitis.

Patients for receiving the compositions of the invention may be any age, but one target population is adolescents (e.g. aged between 10 and 18 years), particularly for booster use. Older (i.e. 18 years and older) or younger (i.e. 10 years or younger) patients may also receive the compositions.

In order to have full efficacy, a typical primary immunization schedule for a child may involve administering more than one dose. For example, doses may be at: 0, 2 and 4 months (time 0 being the first dose); 0, 1 and 2 months; 0 and 2 months; 0, 2 and 8 months; etc. The first dose (time 0) may be administered at about 2 months of age, or sometimes (e.g. in a 0-2-8 month schedule) at around 3 months of age. For booster use, however, a single dose is usually adequate.

Compositions of the invention can be administered by intramuscular injection e.g. into the arm, leg or buttock.

Where compositions of the invention include an aluminium-based adjuvant, settling of components may occur during storage. Aqueous compositions should therefore be shaken before and after reconstitution, prior to administration to a patient.

Conjugation

The invention uses meningococcal conjugates in which capsular saccharides are conjugated to carrier proteins. Useful carrier proteins for covalent conjugation are bacterial toxins or toxoids, such as diphtheria toxoid or tetanus toxoid, or derivatives thereof such as the CRM197 diphtheria toxin mutant [38-40]. Other suitable carrier proteins include the N. meningitidis outer membrane protein [41], synthetic peptides [42,43], heat shock proteins [44,45], pertussis proteins [46,47], cytokines [48], lymphokines [48], hormones [48], growth factors [48], artificial proteins comprising multiple human $CD4^+$ T cell epitopes from various pathogen-derived antigens [49] such as N19 [50], protein D from H. influenzae [51-53], pneumolysin [54] or its non-toxic derivatives [55], pneumococcal surface protein PspA [56], iron-uptake proteins [57], toxin A or B from C. difficile [58], recombinant Pseudomonas aeruginosa exoprotein A (rEPA) [59], etc.

Diphtheria toxoid (Dt), tetanus toxoid (Tt) and CRM197 are the main carriers currently in use in pediatric vaccines e.g. the Hib conjugates from GSK (e.g. as present in HIBERIX™ and INFANRIX HEXA™) use Tt as the carrier, the HIBTITER™ product uses CRM197, the pneumococcal conjugates in PREVENAR™ use CRM197, the MENJUGATE™ and MENINGITEC™ products use CRM197, and NEISVAC-C™ uses Tt.

Conjugates with a saccharide:protein ratio (w/w) of between 1:5 (i.e. excess protein) and 5:1 (i.e. excess saccharide) may be used e.g. ratios between 1:2 and 5:1 and ratios between 1:1.25 and 1:2.5.

Conjugates may be used in conjunction with free carrier protein [60], particularly where the carrier in one or more conjugate(s) is a diphtheria toxoid, tetanus toxoid or pertussis antigen.

The saccharide will typically be activated or functionalised prior to conjugation. Activation may involve, for example, cyanylating reagents such as CDAP (e.g. 1-cyano-4-dimethylamino pyridinium tetrafluoroborate [61,62, etc.]). Other suitable techniques use active esters, carbodiimides, hydrazides, norborane, p-nitrobenzoic acid, N-hydroxysuccinimide, S—NHS, EDC, TSTU; see also the introduction to reference 94). Reductive amination can be used to introduce a reactive amino group.

A process involving the introduction of amino groups into the saccharide (e.g. by replacing terminal =O groups with —$NH_2$) followed by derivatisation with an adipic diester (e.g. adipic acid N-hydroxysuccinimido diester) and reaction with carrier protein can be used. In another useful reaction, a saccharide is derivatised with a cyanylating reagent, followed by coupling to a protein (direct, or after introduction of a thiol or hydrazide nucleophile group into the carrier), without the need to use a linker. Suitable cyanylating reagents include 1-cyano-4-(dimethylamino)-pridinium tetrafluoroborate ('CDAP'), p-nitrophenylcyanate and N-cyanotriethylammonium tetrafluoroborate ('CTEA').

The carrier protein may be covalently conjugated to the saccharide directly or via a linker. Various linkers are known e.g. an adipic acid linker, which may be used by coupling a free —$NH_2$ group (e.g. introduced to a saccharide by reductive amination) with an activated adipic acid (using, for example, diimide activation), and then coupling a protein to the resulting saccharide-adipic acid intermediate [63, 64]. Another type of linkage is a carbonyl linker, which may be formed by reaction of a free hydroxyl group of a modified glucan with CDI [65, 66] followed by reaction with a protein to form a carbamate linkage. Other linkers include β-propionamido [67], nitrophenyl-ethylamine [68], haloacyl halides [69], glycosidic linkages [70], 6-aminocaproic acid [71], N-succinimidyl-3-(2-pyridyldithio)-propionate (SPDP) [72], adipic acid dihydrazide ADH [73], $C_4$ to $C_{12}$ moieties [74], etc. Carbodiimide condensation can also be used [75]. The most preferred link between a carrier and a saccharide is via an adipic acid linker.

Saccharides will typically be covalently linked, either directly or via a linker, to a carrier via a free —$NH_2$ group in the carrier e.g. in a lysine side chain, an arginine side chain or at the N-terminus. Attachment via —SH is also possible e.g. in a cysteine side chain.

CRM197 conjugates of the invention may be obtained as described in reference 33.

As described in reference 76, a mixture can include one conjugate with direct saccharide/protein linkage and another conjugate with linkage via a linker. According to the invention, however, it is preferred that each conjugate includes a linker.

After conjugation, free and conjugated saccharides can be separated. There are many suitable methods for this separation, including hydrophobic chromatography, tangential ultrafiltration, diafiltration, etc. (see also refs. 77 & 78, etc.). If a vaccine comprises a given saccharide in both free and conjugated forms, the unconjugated form is usefully no more than 20% by weight of the total amount of that saccharide in the composition as a whole (e.g. ≤15%, ≤10%, ≤5%, ≤2%, ≤1%).

The amount of carrier (conjugated and unconjugated) from each conjugate may be no more than 100 µg/ml e.g. <30 µg/ml of carrier protein from each conjugate. Some compositions include a total concentration of carrier of less than 500 µg/ml e.g. <400 µg/ml, <300 µg/ml, <200 µg/ml, <100 µg/ml, <50 µg/ml, etc.

Characteristics of Compositions of the Invention

In addition to the antigenic components described above, compositions of the invention (both before and after mixing) will generally include a non-antigenic component. The non-antigenic component can include carriers, adjuvants, excipients, buffers, etc., as described in more detail below.

Compositions of the invention will usually include one or more pharmaceutical carrier(s) and/or excipient(s). Sterile pyrogen-free, phosphate-buffered physiologic saline is a typical carrier. A thorough discussion of pharmaceutically acceptable excipients is available in reference 79.

To control tonicity, it is useful to include a physiological salt, such as a sodium salt. Sodium chloride (NaCl) is one such salt, which may be present at between 1 and 20 mg/ml.

Aqueous compositions (before and/or after reconstitution of lyophilised material) will generally have an osmolality of between 200 mOsm/kg and 400 mOsm/kg e.g. between 240-360 mOsm/kg, or within the range of 290-320 mOsm/kg.

Compositions of the invention may include one or more buffers. Typical buffers include: a phosphate buffer; a Tris buffer; a borate buffer; a succinate buffer; a histidine buffer; or a citrate buffer. Buffers will typically be included in the 5-20 mM range. Such buffers may be included in the aqueous and/or lyophilised components.

The pH of an aqueous composition will generally be between 5.0 and 7.5, and more typically between 5.0 and 6.0 for optimum stability, or between 6.0 and 7.0.

Compositions of the invention are preferably sterile.

Compositions of the invention are preferably non-pyrogenic e.g. containing <1 EU (endotoxin unit, a standard measure) per dose, and preferably <0.1 EU per dose.

Compositions of the invention may be gluten free.

Compositions of the invention may be administered to patients in 0.5 ml doses. References to 0.5 ml doses will be understood to include normal variance e.g. 0.5 ml±0.05 ml. An aqueous component used with the invention may thus have a volume of 0.5 ml.

Adjuvants

Compositions of the invention may include an adjuvant, and this adjuvant may comprise one or more aluminium salts, and particularly an aluminium phosphate adjuvant and/or an aluminium hydroxide adjuvant. Antigenic components used to prepare compositions of the invention may include aluminium adjuvants before being used i.e. they are 'pre-mixed' or 'pre-adsorbed' to the adjuvant(s).

Aluminium adjuvants currently in use are typically referred to either as "aluminium hydroxide" or as "aluminium phosphate" adjuvants. These are names of convenience, however, as neither is a precise description of the actual chemical compound which is present (e.g. see chapter 9 of reference 80). The invention can use any of the "hydroxide" or "phosphate" salts that are in general use as adjuvants.

The adjuvants known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide $Al(OH)_3$, by infrared (IR) spectroscopy, in particular by the presence of an adsorption band at 1070 $cm^{-1}$ and a strong shoulder at 3090-3100 $cm^{-1}$ (chapter 9 of ref. 80).

The adjuvants known as "aluminium phosphate" are typically aluminium hydroxyphosphates, often also containing a small amount of sulfate. They may be obtained by precipitation, and the reaction conditions and concentrations during precipitation can influence the degree of substitution of phosphate for hydroxyl in the salt. Hydroxyphosphates generally have a $PO_4$/Al molar ratio between 0.3 and 0.99. Hydroxyphosphates can be distinguished from strict $AlPO_4$ by the presence of hydroxyl groups. For example, an IR spectrum band at 3164 $cm^{-1}$ (e.g. when heated to 200° C.) indicates the presence of structural hydroxyls (chapter 9 of ref. 80).

The $PO_4/Al^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4$/Al molar ratio between 0.84 and 0.92, included at 0.6 mg $Al^{3+}$/ml. The aluminium phosphate will generally be particulate. Typical diameters of the particles are in the range 0.5-20 µm (e.g. about 5-10 µm) after any antigen adsorption.

The PZC of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

An aluminium phosphate solution used to prepare a composition of the invention may contain a buffer (e.g. a phosphate or a histidine or a Tris buffer), but this is not always necessary. The aluminium phosphate solution is preferably sterile and pyrogen-free. The aluminium phosphate solution may include free aqueous phosphate ions e.g. present at a concentration between 1.0 and 20 mM, preferably between 5 and 15 mM, and more preferably about 10 mM. The aluminium phosphate solution may also comprise sodium chloride. The concentration of sodium chloride is preferably in the range of 0.1 to 100 mg/ml (e.g. 0.5-50 mg/ml, 1-20 mg/ml, 2-10 mg/ml) and is more preferably about 3±1 mg/ml. The presence of NaCl facilitates the correct measurement of pH prior to adsorption of antigens.

Further Antigens that May be Included

As well as including D, T, Pa and conjugated *N. meningitidis* saccharide antigens, compositions may include one or more further antigens. For instance, they may include antigens from other pathogens, particularly from bacteria and/or viruses. Suitable further antigens may be selected from:
- a hepatitis B virus (HBV) surface antigen ('HBsAg')
- inactivated poliovirus vaccine (IPV)
- a capsular saccharide from *Haemophilus influenzae* type B.
- a capsular saccharide from *Streptococcus pneumoniae*.
- a hepatitis A virus (HAV) antigen These antigens may originate from the aqueous or the lyophilised component of the invention.

Hepatitis B Virus Surface Antigen

Hepatitis B virus (HBV) is one of the known agents that cause viral hepatitis. The HBV virion consists of an inner core surrounded by an outer protein coat or capsid, and the viral core contains the viral DNA genome. The major component of the capsid is a protein known as HBV surface antigen or, more commonly, 'HBsAg', which is typically a 226-amino acid polypeptide with a molecular weight of ~24 kDa. All existing hepatitis B vaccines contain HBsAg, and when this antigen is administered to a normal vaccinee it stimulates the production of anti-HBsAg antibodies which protect against HBV infection.

For vaccine manufacture, HBsAg has been made in two ways. The first method involves purifying the antigen in particulate form from the plasma of chronic hepatitis B carriers, as large quantities of HBsAg are synthesized in the liver and released into the blood stream during an HBV infection. The second way involves expressing the protein by recombinant DNA methods. HBsAg for use with the method of the invention is preferably recombinantly expressed in yeast cells. Suitable yeasts include, for example, Saccharomyces (such as S. cerevisiae) or Hanensula (such as H. polymorpha) hosts.

The HBsAg is usually non-glycosylated. Unlike native HBsAg (i.e. as in the plasma-purified product), yeast-expressed HBsAg is generally non-glycosylated, and this is the most preferred form of HBsAg for use with the invention, because it is highly immunogenic and can be prepared without the risk of blood product contamination.

The HBsAg will generally be in the form of substantially-spherical particles (average diameter of about 20 nm), including a lipid matrix comprising phospholipids. Yeast-expressed HBsAg particles may include phosphatidylinositol, which is not found in natural HBV virions. The particles may also include a non-toxic amount of LPS in order to stimulate the immune system [81]. HBsAg may be in the form of particles including a lipid matrix comprising phospholipids, phosphatidylinositol and polysorbate 20.

All known HBV subtypes contain the common determinant 'a'. Combined with other determinants and subdeterminants, nine subtypes have been identified: ayw 1, ayw2, ayw3, ayw4, ayr, adw2, adw4, adrq- and adrq+. Besides these subtypes, other variants have emerged, such as HBV mutants that have been detected in immunised individuals ("escape mutants"). The usual HBV subtype with the invention is subtype adw2.

In addition to the 'S' sequence, a surface antigen may include all or part of a pre-S sequence, such as all or part of a pre-S1 and/or pre-S2 sequence.

Quantities of HBsAg are typically expressed in micrograms, and a typical amount of HBsAg per vaccine dose is between 5 and 25 μg e.g. 10 μg/dose.

Although HBsAg may be adsorbed to an aluminium hydroxide adjuvant in the final vaccine (as in the well-known ENGERIX-B™ product), or may remain unadsorbed, it will generally be adsorbed to an aluminium phosphate adjuvant [82].

When it is used with the invention, HBsAg will typically be in the aqueous component.

Inactivated Poliovirus Vaccine

Poliovirus causes poliomyelitis. Rather than use oral poliovirus vaccine, the invention may use IPV, as disclosed in more detail in chapter 24 of reference 1.

Polioviruses may be grown in cell culture, and a preferred culture uses a Vero cell line, derived from monkey kidney. Vero cells can conveniently be cultured on microcarriers. After growth, virions may be purified using techniques such as ultrafiltration, diafiltration, and chromatography. Prior to administration to patients, polioviruses must be inactivated, and this can be achieved by treatment with formaldehyde.

Poliomyelitis can be caused by one of three types of poliovirus. The three types are similar and cause identical symptoms, but they are antigenically very different and infection by one type does not protect against infection by others. It is therefore preferred to use three poliovirus antigens in the invention: poliovirus Type 1 (e.g. Mahoney strain), poliovirus Type 2 (e.g. MEF-1 strain), and poliovirus Type 3 (e.g. Saukett strain). Sabin strains may also be used (e.g. see references 83 & 84). The viruses are preferably grown, purified and inactivated individually, and are then combined to give a bulk trivalent mixture for use with the invention.

Quantities of IPV are typically expressed in the 'DU' unit (the "D-antigen unit" [85]). It is usual to include between 1-100 DU per viral type per dose e.g. about 80 DU/ml of Type 1 poliovirus, about 16 DU/ml of type 2 poliovirus, and about 64 DU/ml of type 3 poliovirus. Lower doses can also be used, however, as disclosed in reference 86.

Poliovirus antigens are preferably not adsorbed to any aluminium salt adjuvant before being used to make compositions of the invention, but they may become adsorbed onto aluminum adjuvant(s) in the vaccine composition during storage.

When it is used with the invention, IPV will typically be in the aqueous component.

Hib Saccharides

The capsular saccharide antigen from H. influenzae type B ('Hib') is well known [e.g. chapter 14 of reference 1] and its preparation is well documented [e.g. references 87 to 96]. The Hib saccharide is conjugated to a carrier protein in order to enhance its immunogenicity, especially in children. The invention may use any suitable Hib conjugate.

The saccharide moiety of the Hib conjugate may be a polysaccharide (e.g. full-length polyribosylribitol phosphate (PRP)), but it is also possible to use oligosaccharides (e.g. MW from ~1 to ~5 kDa). Oligosaccharides are conveniently formed by fragmentation of purified PRP (e.g. by hydrolysis), which will usually be followed by purification of the fragments of the desired size. Where the composition of the invention includes a conjugated oligosaccharide, the preparation of oligosaccharides should precede conjugation.

The concentration of Hib conjugate in compositions of the invention will usually be in the range of 0.5 μm/ml to 50 μg/ml e.g. from 1 μg/ml to 20 μg/ml, from 12 μg/ml to 16 μg/ml, etc. The concentration may be about 15 or about 12.5 μg/ml in some embodiments. A mass of less than 5 μg per dose may be suitable [97] e.g. in the range 1-5 μg, 2-4 μm, or about 2.5 μg. As described below, the dose of Hib saccharide may be selected based on the dose of the meningococcal saccharide (in particular, with multiple meningococcal serogroups, their mean mass). Further characteristics of Hib conjugates are as disclosed above for meningococcal conjugates, including choice of carrier protein (e.g. CRM197 or tetanus toxoid), linkages, ratios, etc.

A Hib conjugate may be adsorbed to an aluminium salt or may be unadsorbed. Adsorption to aluminium phosphate adjuvants has been reported to be advantageous in some circumstances [98], whereas non-adsorption has been reported to be advantageous in other circumstances [3]. These possibilities can easily be investigated and compared for any particular combination.

Various different Hib conjugates are known. For instance, Table 14-7 of reference 1 gives the characteristics of four different Hib conjugates. These differ by various parameters e.g. carrier protein. The invention can use any suitable carrier protein (see below), such as CRM197 (as in 'HbOC'), tetanus toxoid (as in 'PRP-T') and the outer membrane complex of N. meningitidis (as in 'PRP-OMP').

When a composition of the invention includes saccharide from more than one meningococcal serogroup, there is a mean saccharide mass per serogroup. If substantially equal masses of each serogroup are used then the mean mass will be the same as each individual mass; where non-equal masses are used then the mean will differ e.g. with a 10:5:5:5 μg amount for a MenACWY mixture, the mean mass is 6.25 μg per serogroup. If a Hib saccharide is also included then, in some embodiments, its mass will be substantially the same as the mean mass of meningococcal saccharide per serogroup. In some embodiments, the mass of Hib saccharide will be more than (e.g. at least 1.5×) the mean mass of meningococcal saccharide per serogroup. In some embodiments, the mass of Hib saccharide will be less than (e.g. by at least 1.5×) the mean mass of meningococcal saccharide per serogroup [99].

When it is used with the invention, a Hib conjugate may be in the aqueous component or the lyophilised component. Often it will be in the lyophilised component.

Pneumococcal Saccharides

Conjugated pneumococcal antigens comprise capsular saccharide antigens from Streptococcus pneumoniae conjugated to carrier proteins [e.g. refs. 100 to 102]. It is normal to include saccharides from more than one serotype of S. pneumoniae: mixtures of polysaccharides from 23 different serotype are widely used, as are conjugate vaccines with polysaccharides from between 5 and 11 different serotypes [103]. For example, PREVNAR™ [104] contains antigens from seven serotypes (4, 6B, 9V, 14, 18C, 19F, and 23F) with each saccharide individually conjugated to CRM197 by reductive amination, with 2 μg of each saccharide per 0.5 ml dose (4 μg of serotype 6B).

Compositions of the invention may include saccharide antigens for at least serotypes 6B, 14, 19F and 23F. Further serotypes may be selected from: 1, 3, 4, 5, 7F, 9V and 18C. 7-valent (as in PREVNAR™), 9-valent (e.g. the 7 serotypes from PREVNAR, plus 1 & 5), 10-valent (e.g. the 7 serotypes from PREVNAR, plus 1, 5 & 7F) and 11-valent (e.g. the 7 serotypes from PREVNAR, plus 1, 3, 5 & 7F) coverage of pneumococcal serotypes is particularly useful. A 13-valent combination of serotypes 1, 3, 4, 5, 6A, 6B, 7F, 9V, 14, 18C, 19A, 19F and 23F is advantageous.

Further characteristics of pneumococcal conjugates are as disclosed above for meningococcal conjugates, including choice of carrier protein (e.g. CRM197 or tetanus toxoid), linkages, ratios, etc. Where a composition includes more than one conjugate, each conjugate may use the same carrier protein or a different carrier protein. Reference 105 describes potential advantages when using different carrier proteins in multivalent pneumococcal conjugate vaccines.

Typically, a composition will include between 1 μg and 20 μg (measured as saccharide) per dose of each serotype that is present.

When used with the invention, pneumococcal conjugate(s) may be in the aqueous component or the lyophilised component.

Hepatitis A Virus Antigens

Hepatitis A virus (HAV) is one of the known agents that cause viral hepatitis. HAV vaccines are disclosed in chapter 15 of reference 1. A useful HAV component is based on inactivated virus, and inactivation can be achieved by formalin treatment. Virus can be grown on human embryonic lung diploid fibroblasts, such as MRC-5 cells. A useful HAV strain is HM175, although CR326F can also be used. The cells can be grown under conditions that permit viral growth. The cells are lysed, and the resulting suspension can be purified by ultrafiltration and gel permeation chromatography.

The amount of HAV antigen, measured in EU (Elisa Units), is typically at least about 500 EU/ml.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Concentrations of conjugates are defined herein in tennis of mass of saccharide, in order to avoid variation due to choice of carrier.

Where an antigen is described as being "adsorbed" to an adjuvant, it is preferred that at least 50% (by weight) of that antigen is adsorbed e.g. 50%, 60%, 70%, 80%, 90%, 95%, 98% or more. It is preferred that diphtheria toxoid and tetanus toxoid are both totally adsorbed i.e. none is detectable in supernatant. Total adsorption of HBsAg is also preferred.

Where animal (and particularly bovine) materials are used in the culture of cells, they should be obtained from sources that are free from transmissible spongiform encaphalopathies (TSEs), and in particular free from bovine spongiform encephalopathy (BSE).

MODES FOR CARRYING OUT THE INVENTION

Capsular saccharides are purified from meningococci from serogroups A, C, W135 and Y following the procedures disclosed in references 19 and 33. They are conjugated to CRM197 following the procedures disclosed in references 19 and 33. In alternative embodiments they are conjugated to tetanus toxoid.

The conjugates are mixed and then lyophilised to give final amounts per dose of 12 μg MenA and 6 μg of each of MenC, MenW135 and MenY. Sucrose is included at 30 mg/dose for stabilisation.

The total and free saccharide contents of each of the CRM-MenA, CRM-MenC, CRM-MenY and CRM-MenW conjugates were confirmed using high performance anion exchange chromatography coupled with pulsed amperometric detection (HPAEC-PAD) and by colorimetric methods. Molecular size distribution was determined using size exclusion chromatography coupled to PAD and capillary zone electrophoresis (CZE), to monitor the integrity of these conjugates after lyophilisation. The results indicated that lyophilisation did not have any negative impact on saccharide content or molecular size distribution of the glycoconjugates when compared to pre-lyophilised conjugates.

NMR was also used to analyse the identity and stability conjugates, both on monovalent bulks and also in the final combined mixture (after reconstitution into aqueous form). Since each lyophilized combination contains a large excess of sucrose, samples were dialysed at 4° C. for 48 hours with four changes of 10 mM sodium phosphate buffer, pH 7.2 to remove the sucrose.

An identity test was developed by selecting a 0.7 ppm restricted window (from the down-field value at 5.6 ppm to the up-field value at 4.9 ppm) where the proton anomeric signals of the meningococcal conjugates were detected and assigned. Selecting a restricted spectral region, the assay was very simple but could identify all the conjugated polysaccharide antigens in the combined vaccine, detecting two signals for MenA and one signal for each of MenC, MenW135 and MenY.

The combined 4-valent conjugate lyophilisate is reconstituted with an aqueous vaccine such as BOOSTRIX™, KINRIX™ or ADACEL™.

In different experiments quadrivalent meningococcal 4-valent MenACWY conjugated vaccine with CRM197 carrier was administered to adolescents at the same time as BOOSTRIX™. In this single centre Phase III study, 1620 subjects 11-18 years of age, received the 4-valent meningococcal vaccine at the same time as BOOSTRIX™. Meningococcal serogroup-specific serum bactericidal activities (SBA), and antibodies to Tdap antigens, were determined before and 1 month after the respective vaccinations. Proportions of subjects with SBA titres ≥0.1:8 for all four serogroups (A, C, W-135, Y) were non-inferior compared to patient receiving Men-ACWY conjugate vaccine alone. Immune responses to the BOOSTRIX™ antigens were comparable to those achieved when the vaccine was given alone, although the increases in anti-FHA and anti-PRN titres were lower. There was a notable increase in anti-diphtheria responses when the vaccines were administered at the same time, probably due to the presence of CRM197 in the meningococcal conjugate component.

It will be understood that the invention will be described by way of example only, and that modifications may be made whilst remaining within the scope and spirit of the invention.

REFERENCES

[1] Vaccines. (eds. Plotkin & Orenstein). 4th edition, 2004, ISBN: 0-7216-9688-0.
[2] WO2006/097851.
[3] WO02/00249.
[4] WO02/080965.
[5] WO2006/075170.
[6] Minh et al. (1999) *Pediatrics* 104:70-76.
[7] Theeten et al. (2005) *Vaccine* 23:1515-21.
[8] Rappuoli et al. (1991) *TIBTECH* 9:232-238.
[9] Nencioni et al. (1991) *Infect Immun.* 59(2): 625-30.
[10] Module 1 of WHO's *The immunological basis for immunization series* (Galazka).
[11] NIBSC code: 69/017.
[12] NIBSC code: DIET.
[13] NIBSC code: TEFT.
[14] *W.H.O. Tech. Rep. Ser.* 594:51, 1976.
[15] Jones (2001) *Curr Opin Investig Drugs* 2:47-49.
[16] Costantino et al. (1992) *Vaccine* 10:691-8.
[17] Lieberman et al. (1996) *JAMA* 275:1499-503.
[18] WO02/058737.
[19] WO03/007985.
[20] Rennels et al. (2002)*Pediatr Infect Dis J* 21:978-979.
[21] Campbell et al. (2002) *J Infect Dis* 186:1848-1851.
[22] WO03/080678.
[23] Glode et al. (1979) *J Infect Dis* 139:52-56
[24] WO94/05325; U.S. Pat. No. 5,425,946.
[25] Arakere & Frasch (1991) *Infect. Immun.* 59:4349-4356.
[26] Michon et al. (2000) *Dev. Biol.* 103:151-160.
[27] Rubinstein & Stein (1998) *J. Immunol.* 141:4357-4362.
[28] WO2005/033148.
[29] WO2007/000314.
[30] WO2007/000341.
[31] WO2008/011201.
[32] WO2004/067030.
[33] Bardotti et al. (2008) *Vaccine* 26:2284-96.
[34] Bröker et al. (2009) *Vaccine* 27:5574-80.
[35] Knuf et al. (2009) *Vaccine doi:* 10.1016/j.vaccine.2009.10.064.
[36] Pozsgay (2008)*Curr Top Med Chem* 8:126-140.
[37] Berkin et al. (2002)*Chemistry* 8:4424-33.
[38] Anonymous (January 2002) *Research Disclosure*, 453077.
[39] Anderson (1983) *Infect Immun* 39(1):233-238.
[40] Anderson et al. (1985) *J Clin Invest* 76(1):52-59.
[41] EP-A-0372501.
[42] EP-A-0378881.
[43] EP-A-0427347.
[44] WO93/17712
[45] WO94/03208.
[46] WO98/58668.
[47] EP-A-0471177.
[48] WO91/01146
[49] Falugi et al. (2001) *Eur J Immunol* 31:3816-3824.
[50] Baraldo et al. (2004) *Infect Immun* 72(8):4884-7.
[51] EP-A-0594610.
[52] Ruan et al. (1990) *J Immunol* 145:3379-3384.
[53] WO00/56360.
[54] Kuo et al. (1995) *Infect Immun* 63:2706-13.
[55] Michon et al. (1998) *Vaccine.* 16:1732-41.
[56] WO02/091998.
[57] WO01/72337
[58] WO00/61761.
[59] WO00/33882
[60] WO96/40242
[61] Lees et al. (1996) *Vaccine* 14:190-198.
[62] WO95/08348.
[63] *Mol. Immunol.,* 1985, 22, 907-919
[64] EP-A-0208375
[65] Bethell G. S. et al., *J. Biol. Chem.,* 1979, 254, 2572-4
[66] Hearn M. T. W., *J. Chromatogr.,* 1981, 218, 509-18
[67] WO00/10599
[68] Geyer et al., *Med. Microbiol. Immunol,* 165: 171-288 (1979).
[69] U.S. Pat. No. 4,057,685.
[70] U.S. Pat. Nos. 4,673,574; 4,761,283; 4,808,700.
[71] U.S. Pat. No. 4,459,286.
[72] U.S. Pat. No. 5,204,098
[73] U.S. Pat. No. 4,965,338
[74] U.S. Pat. No. 4,663,160.
[75] WO2007/000343.
[76] WO2007/000342.
[77] Lei et al. (2000) *Dev Biol (Basel)* 103:259-264.
[78] WO00/38711; U.S. Pat. No. 6,146,902.
[79] Gennaro (2000) *Remington: The Science and Practice of Pharmacy.* 20th edition, ISBN: 0683306472.
[80] *Vaccine Design: The Subunit and Adjuvant Approach* (eds. Powell & Newman) Plenum Press 1995 (ISBN 0-306-44867-X).
[81] Vanlandschoot et al. (2005) *J Gen Virol* 86:323-31.

[82] WO93/24148.
[83] WO2007/007344.
[84] WO2008/044611.
[85] Module 6 of WHO's *The immunological basis for immunization series* (Robertson)
[86] WO2008/028957.
[87] Ramsay et al. (2001) *Lancet* 357(9251):195-6.
[88] Lindberg (1999) *Vaccine* 17 Suppl 2:S28-36.
[89] Buttery & Moxon (2000) *J R Coll Physicians Lond* 34:163-168.
[90] Ahmad & Chapnick (1999) *Infect Dis Clin North Am* 13:113-133, vii.
[91] Goldblatt (1998) *J. Med. Microbiol.* 47:563-567.
[92] European patent 0477508.
[93] U.S. Pat. No. 5,306,492.
[94] WO98/42721.
[95] *Conjugate Vaccines* (eds. Cruse et al.) ISBN 3805549326, particularly vol. 10:48-114.
[96] Hermanson (1996) *Bioconjugate Techniques* ISBN: 0123423368 or 012342335X.
[97] WO2007/000327.
[98] WO97/00697.
[99] WO2007/000322.
[100] Watson (2000) *Pediatr Infect Dis J* 19:331-332.
[101] Rubin (2000) *Pediatr Clin North Am* 47:269-285, v.
[102] Jedrzejas (2001) *Microbiol Mol Biol Rev* 65:187-207.
[103] Zielen et al. (2000) *Infect. Immun.* 68:1435-1440.
[104] Darkes & Plosker (2002) *Paediatr Drugs* 4:609-630.
[105] WO2007/071707

The invention claimed is:

1. A kit comprising: (i) an aqueous component, comprising a mixture of diphtheria toxoid, tetanus toxoid and acellular pertussis antigens, in which the concentration of diphtheria toxoid is <10 flocculation value/ml (Lf/ml); and (ii) a lyophilised component, comprising a conjugate of a *Neisseria meningitidis* capsular saccharide, wherein the aqueous component and the lyophilised component are formulated to be combined into a combined vaccine and the *Neisseria meningitidis* capsular saccharide is conjugated to a CRM197 carrier protein, a tetanus toxoid carrier protein, or a diphtheria toxoid carrier protein.

2. The kit of claim 1, wherein the aqueous component includes an adjuvant.

3. The kit of claim 2, wherein the adjuvant comprises one or more aluminium salts.

4. The kit of claim 3, wherein the aqueous component has an aluminium concentration less than 0.84 mg/ml.

5. The kit of claim 1, wherein the concentration of diphtheria toxoid in the aqueous component is 4 Lf/ml or 5 Lf/ml.

6. The kit of claim 1, wherein the concentration of tetanus toxoid in the aqueous component is 10 Lf/ml.

7. The kit of claim 1, wherein the ratio of diphtheria toxoid to tetanus toxoid in the aqueous component is 1:2 or 1:2.5, as measured in Lf units.

8. The kit of claim 1, wherein the acellular pertussis antigen in the aqueous component comprises inactivated pertussis toxin ('PT'), filamentous hemagglutinin ('FHA') and pertactin.

9. The kit of claim 8, wherein the concentration of PT in the aqueous component is less than 25 µg/ml.

10. The kit of claim 8, wherein the concentration of pertussis toxoid in the aqueous component is 5 µg/ml or 16µg/ml.

11. The kit of claim 8, wherein the concentration of FHA in the aqueous component is 10 µg/ml or 16 µg/ml.

12. The kit of claim 8, wherein the concentration of pertactin in the aqueous component is 5 µg/ml or 6 µg/ml.

13. The kit of claim 8, wherein the weight ratios of PT:FHA:pertactin are 16:16:5 or 5:10:6.

14. The kit of claim 3, wherein diphtheria toxoid, tetanus toxoid and acellular pertussis antigens in the aqueous component are absorbed to aluminium hydroxide.

15. The kit of claim 3, wherein diphtheria toxoid, tetanus toxoid and acellular pertussis antigens in the aqueous component are adsorbed to aluminium phosphate.

16. The kit of claim 1, wherein the aqueous component is mercury-free and includes between 4-7mg/ml 2-phenoxyethanol.

17. The kit of claim 1, wherein the aqueous component is preservative-free.

18. The kit of claim 1, wherein the aqueous component is free from meningococcal capsular saccharide(s).

19. The kit of claim 1, wherein the lyophilized component includes conjugated capsular saccharides from serogroups A and C of *Neisseria meningitidis*.

20. The kit of claim 19, wherein the mass ratio of saccharides from serogroups A and C is 1:1 or 2:1 (A:C).

21. The kit of claim 1, wherein the lyophilized component includes conjugated capsular saccharides from serogroups C and Y of *Neisseria meningitidis*.

22. The kit of claim 21, wherein the mass ratio of saccharides from serogroups C and Y is 1:1 or 2:1 or 1:2 (C:Y).

23. The kit of claim 1, wherein the lyophilized component includes conjugated capsular saccharides from serogroups A, C, W135 and Y of *Neisseria meningitidis*.

24. The kit of claim 23, wherein the mass ratio of saccharides from serogroups A, C, W135 and Y is 1:1:1:1, 2:1:1:1, 1:4:1:1, 1:2:1:1 or 2:2:1:1 (A:C:W135:Y).

25. The kit of claim 19, wherein the mass of capsular saccharide per vaccine dose is 2.5 µg/serogroup, 4 µg/serogroup, 5 µg/serogroup or 10 µg/serogroup, and wherein the mass from each serogroup may be the same or different.

26. The kit of claim 1, wherein at least one *Neisseria meningitides* capsular saccharide conjugate in the lyophilized component has the CRM197 carrier protein.

27. The kit of claim 26, wherein all *Neisseria meningitidis* capsular saccharide conjugates in the lyophilized component have CRM197 carrier proteins.

28. The kit of claim 1, wherein at least one *Neisseria meningitides* capsular saccharide conjugate in the lyophilized component has the tetanus toxoid carrier protein.

29. The kit of claim 28, wherein all *Neisseria meningitidis* capsular saccharide conjugates in the lyophilized component have tetanus toxoid carrier proteins.

30. The kit of claim 1, wherein the lyophilized component includes a lyophilisation stabiliser.

31. The kit of claim 30, wherein the lyophilisation stabiliser comprises lactose, sucrose, trehalose or mannitol.

32. The kit of claim 1, wherein lyophilized component includes sodium chloride.

33. The kit of claim 1, wherein the lyophilized component includes an adjuvant.

34. The kit of claim 1, wherein the lyophilized component does not include an additional adjuvant.

35. The kit of claim 1, wherein the lyophilized component is free from pertussis antigen(s).

36. The kit of claim 1, wherein the aqueous component includes an inactivated poliovirus vaccine (IPV).

37. The kit of claim 1, wherein the lyophilized component includes a conjugated capsular saccharide from *Haemophilus influenzae*.

38. The kit of claim 37, wherein the capsular saccharide from *Haemophilus influenza* is presented at a mass of 5 µg or 10 µg for every ml of aqueous component.

39. The kit of claim 1 wherein the aqueous component and the lyophilized component are present in amounts sufficient for a single dose of the combined vaccine.

40. A kit comprising: (i) an aqueous component, comprising a mixture of diphtheria toxoid, tetanus toxoid and acellular pertussis antigens, in which the concentration of tetanus toxoid is <15 Lf/ml; and (ii) a lyophilised component, comprising a conjugate of a Neisseria meningitidis capsular saccharide, wherein the aqueous component and the lyophilised component are formulated to be combined into a combined vaccine and the *Neisseria meningitidis* capsular saccharide is conjugated to a CRM197 carrier protein, a tetanus toxoid carrier protein, or a diphtheria toxoid carrier protein.

41. The kit of claim 40 wherein the aqueous component and the lyophilized component are present in amounts sufficient for a single dose of the combined vaccine.

42. A kit comprising: (i) an aqueous component, comprising a mixture of diphtheria toxoid, tetanus toxoid and acellular pertussis antigens, in which the concentration of diphtheria toxoid is <10 Lf/ml and the concentration of tetanus toxoid is <15 Lf/ml; and (ii) a lyophilised component, comprising a conjugate of a *Neisseria meningitidis* capsular saccharide, wherein the aqueous component and the lyophilised component are formulated to be combined into a combined vaccine and the *Neisseria meningitidis* capsular saccharide is conjugated to a CRM197 carrier protein, a tetanus toxoid carrier protein, or a diphtheria toxoid carrier protein.

43. The kit of claim 42 wherein the aqueous component and the lyophilized component are present in amounts sufficient for a single dose of the combined vaccine.

* * * * *

UNITED STATES PATENT AND TRADEMARK OFFICE
CERTIFICATE OF CORRECTION

PATENT NO.       : 9,511,132 B2
APPLICATION NO. : 13/139021
DATED            : December 6, 2016
INVENTOR(S)      : Mario Contorni It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 40 days.

Signed and Sealed this

Twenty-fifth Day of September, 2018

Andrei Iancu
*Director of the United States Patent and Trademark Office*